United States Patent
Hnojewyj

(10) Patent No.: US 8,383,144 B2
(45) Date of Patent: *Feb. 26, 2013

(54) TISSUE ADHERING COMPOSITIONS

(75) Inventor: Olexander Hnojewyj, Saratoga, CA (US)

(73) Assignee: Neomend, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/641,215

(22) Filed: Dec. 17, 2009

(65) Prior Publication Data

US 2010/0173843 A1 Jul. 8, 2010

Related U.S. Application Data

(60) Continuation of application No. 12/004,964, filed on Dec. 21, 2007, which is a continuation of application No. 10/972,259, filed on Oct. 22, 2004, now Pat. No. 7,318,933, which is a division of application No. 09/780,014, filed on Feb. 9, 2001, now Pat. No.

(Continued)

(51) Int. Cl.
*A61B 17/04* (2006.01)

(52) U.S. Cl. ...... 424/426; 424/486; 514/1.1; 514/21.92; 606/214

(58) Field of Classification Search .................. None
See application file for complete search history.

(56) References Cited

U.S. PATENT DOCUMENTS

| | | | |
|---|---|---|---|
| 4,101,380 A | 7/1978 | Rubinstein et al. | |
| 4,161,948 A | 7/1979 | Bichon | |
| 4,464,468 A | 8/1984 | Avrameas et al. | |
| 4,839,345 A | 6/1989 | Doi et al. | |
| 5,051,292 A | 9/1991 | Katoh et al. | |
| 5,051,406 A | 9/1991 | Satoh | |
| 5,129,882 A | 7/1992 | Weldon et al. | |
| 5,137,818 A | 8/1992 | Harder et al. | |
| 5,207,670 A | 5/1993 | Sinofsky | |
| 5,252,714 A | 10/1993 | Harris et al. | |
| 5,318,524 A | 6/1994 | Morse et al. | |
| 5,383,896 A | 1/1995 | Gershony et al. | |
| 5,403,278 A | 4/1995 | Ernst et al. | |
| 5,410,016 A | 4/1995 | Hubbell et al. | |

(Continued)

FOREIGN PATENT DOCUMENTS

| | | |
|---|---|---|
| EP | 1107813 B1 | 5/2006 |
| JP | 8024325 A | 1/1996 |

(Continued)

OTHER PUBLICATIONS

West, J.L., et al., Proteolytically Degradable Hydrogels, Apr. 30-May 4, 1997, 23rd Annual Meeting of the Society for Biomaterials, New Orleans, Louisiana.

(Continued)

*Primary Examiner* — Jeffrey E Russel
(74) *Attorney, Agent, or Firm* — Pepper Hamilton LLP

(57) ABSTRACT

A method mixes a first component, a second component, and a buffer material. The first component includes an electrophilic polymer material comprising poly(ethylene glycol) having a functionality of at least three. The second component includes a nucleophilic material comprising a natural or synthetic protein at a concentration of about 25% or less that, when mixed with the first component within a reaction pH range, cross-links with the first component to form a non-liquid, three-dimensional barrier. The buffer material includes tris-hydroxymethylaminomethane having a pH within the reaction pH range. The method applies the mixture to adhere to a tissue region.

14 Claims, 6 Drawing Sheets

Related U.S. Application Data 6,830,756, which is a continuation-in-part of application No. 09/283,535, filed on Apr. 1, 1999, now Pat. No. 6,458,147, which is a continuation-in-part of application No. 09/188,083, filed on Nov. 6, 1998, now Pat. No. 6,371,975.

(56) References Cited

U.S. PATENT DOCUMENTS

| | | | |
|---|---|---|---|
| 5,419,765 | A | 5/1995 | Weldon et al. |
| 5,514,379 | A | 5/1996 | Weissleder et al. |
| 5,520,885 | A | 5/1996 | Coelho et al. |
| 5,529,577 | A | 6/1996 | Hammerslag |
| 5,567,435 | A | 10/1996 | Hubbell et al. |
| 5,583,114 | A | 12/1996 | Barrows et al. |
| 5,601,602 | A | 2/1997 | Fowler |
| 5,618,790 | A | 4/1997 | Kennedy et al. |
| 5,626,601 | A | 5/1997 | Gershony et al. |
| 5,626,863 | A | 5/1997 | Hubbell et al. |
| 5,653,730 | A | 8/1997 | Hammerslag |
| 5,672,662 | A | 9/1997 | Harris et al. |
| 5,676,689 | A | 10/1997 | Kensey et al. |
| 5,725,498 | A | 3/1998 | Janzen et al. |
| 5,733,563 | A | 3/1998 | Fortier |
| 5,739,208 | A | 4/1998 | Harris |
| 5,752,974 | A | 5/1998 | Rhee et al. |
| 5,759,194 | A | 6/1998 | Hammerslag |
| 5,782,860 | A | 7/1998 | Epstein et al. |
| 5,791,352 | A | 8/1998 | Reich et al. |
| 5,824,015 | A | 10/1998 | Sawyer |
| 5,843,124 | A | 12/1998 | Hammerslag |
| 5,844,016 | A | 12/1998 | Sawhney et al. |
| 5,858,746 | A | 1/1999 | Hubbell et al. |
| 5,874,500 | A | 2/1999 | Rhee et al. |
| 5,900,245 | A | 5/1999 | Sawhney et al. |
| 5,900,461 | A | 5/1999 | Harris |
| 5,922,009 | A | 7/1999 | Epstein et al. |
| 5,932,462 | A | 8/1999 | Harris et al. |
| 5,935,147 | A | 8/1999 | Kensey et al. |
| 5,936,035 | A | 8/1999 | Rhee et al. |
| 5,942,209 | A | 8/1999 | Leavitt et al. |
| 5,951,583 | A | 9/1999 | Jensen et al. |
| 5,951,589 | A | 9/1999 | Epstein et al. |
| 5,962,649 | A * | 10/1999 | Noda et al. ............ 530/364 |
| 5,986,043 | A | 11/1999 | Hubbell et al. |
| 5,990,237 | A | 11/1999 | Bentley et al. |
| 6,007,613 | A | 12/1999 | Izoret |
| 6,022,361 | A | 2/2000 | Epstein et al. |
| 6,033,424 | A | 3/2000 | Ouchi |
| 6,033,427 | A | 3/2000 | Lee |
| 6,051,248 | A | 4/2000 | Sawhney et al. |
| 6,060,582 | A | 5/2000 | Hubbell et al. |
| 6,083,524 | A | 7/2000 | Sawhney et al. |
| 6,116,130 | A | 9/2000 | Cogan |
| 6,140,089 | A | 10/2000 | Aebischer et al. |
| 6,152,943 | A | 11/2000 | Sawhney |
| 6,162,241 | A | 12/2000 | Coury et al. |
| 6,165,201 | A | 12/2000 | Sawhney et al. |
| 6,177,095 | B1 | 1/2001 | Sawhney et al. |
| 6,179,862 | B1 | 1/2001 | Sawhney |
| 6,302,898 | B1 | 10/2001 | Edwards et al. |
| 6,303,111 | B1 | 10/2001 | Maurer et al. |
| 6,312,725 | B1 | 11/2001 | Wallace et al. |
| 6,371,975 | B2 | 4/2002 | Cruise et al. |
| 6,379,373 | B1 | 4/2002 | Sawhney et al. |
| 6,458,147 | B1 | 10/2002 | Cruise et al. |
| 6,495,127 | B1 | 12/2002 | Wallace et al. |
| 6,514,534 | B1 | 2/2003 | Sawhney |
| 6,586,586 | B1 * | 7/2003 | Krotz et al. ............ 536/25.4 |
| 6,830,756 | B2 | 12/2004 | Hnohewyj |
| 6,858,409 | B1 * | 2/2005 | Thompson et al. ......... 435/69.7 |
| 6,899,889 | B1 | 5/2005 | Hnojewyj et al. |
| 7,057,019 | B2 | 6/2006 | Pathak |
| 7,247,314 | B2 | 7/2007 | Hnojewyj et al. |
| 7,318,933 | B2 | 1/2008 | Hnohewyj |
| 7,351,249 | B2 | 4/2008 | Hnojewyj et al. |
| 8,034,367 | B2 * | 10/2011 | Hnojewyj ............ 424/426 |
| 2008/0108577 | A1 | 5/2008 | Hnohewyj |

FOREIGN PATENT DOCUMENTS

| | | |
|---|---|---|
| WO | WO 93/00890 | 1/1993 |
| WO | WO 93/17669 A1 | 9/1993 |
| WO | WO 94/03155 A1 | 2/1994 |
| WO | WO 94/23743 | 10/1994 |
| WO | WO 95/13312 | 5/1995 |
| WO | WO96/11671 | 4/1996 |
| WO | WO 96/21469 A1 | 7/1996 |
| WO | WO97/22371 | 6/1997 |
| WO | WO 98/12274 A1 | 3/1998 |
| WO | WO 98/35631 A1 | 8/1998 |
| WO | WO99/07417 | 2/1999 |
| WO | WO99/14259 | 3/1999 |
| WO | WO 99/22770 | 5/1999 |
| WO | WO 99/31167 A1 | 6/1999 |
| WO | WO99/45964 | 9/1999 |
| WO | WO 99/55355 | 11/1999 |
| WO | WO00/09087 | 2/2000 |
| WO | WO00/09199 | 2/2000 |
| WO | WO 00/12018 A1 | 3/2000 |
| WO | WO 00/33764 | 6/2000 |
| WO | WO00/33764 | 6/2000 |
| WO | WO00/62827 | 10/2000 |
| WO | WO 01/16210 A1 | 3/2001 |

OTHER PUBLICATIONS

Kurisawa, et al., Double-stimuli-responsive degradation of hydrogels consisting of oligopeptide-terminated poly(ethylene glycol) and dextran with an interpenetrating polymer network, *Journal of Biomaterials Science, Polymer Edition*, 1997, 8(9):691-708.

Nimni, et al., Chemically Modified Collagen: A Natural Biomaterial for Tissue Replacement, *Journal of Biomedical Materials Research*, Jun. 1987, 21(6):741-771.

* cited by examiner

TISSUE ADHERING COMPOSITIONS

RELATED APPLICATIONS

This application is a continuation of co-pending U.S. patent application Ser. No. 12/004,964, filed Dec. 21, 2007, which is a continuation of co-pending U.S. patent application Ser. No. 10/972,259, filed Oct. 22, 2004, now U.S. Pat. No. 7,318,933, issued Jan. 15, 2008, which is a divisional of U.S. patent application Ser. No. 09/780,014, filed Feb. 9, 2001, now U.S. Pat. No. 6,830,756, issued Dec. 14, 2004, which is a continuation-in-part of U.S. patent application Ser. No. 09/283,535, filed Apr. 1, 1999, now U.S. Pat. No. 6,458,147, issued Oct. 1, 2002, which is itself a continuation-in-part of U.S. patent application Ser. No. 09/188,083, filed Nov. 6, 1998, now U.S. Pat. No. 6,371,975, issued Apr. 16, 2002.

FIELD OF THE INVENTION

The invention generally relates to the composition of biocompatible materials and their application to body tissue to affect desired therapeutic results.

BACKGROUND OF THE INVENTION

There are many therapeutic indications today that pose problems in terms of technique, cost efficiency, or efficacy, or combinations thereof.

For example, following an interventional procedure, such as angioplasty or stent placement, a 5 Fr to 8 Fr arteriotomy remains. Typically, the bleeding from the arteriotomy is controlled through pressure applied by hand, by sandbag, or by C-clamp for at least 30 minutes. While pressure will ultimately achieve hemostasis, the excessive use and cost of health care personnel is incongruent with managed care goals.

Various alternative methods for sealing a vascular puncture site have been tried. For example, collagen plugs have been used to occlude the puncture orifice. The collagen plugs are intended to activate platelets and accelerate the natural healing process. Holding the collagen seals in place using an anchor located inside the artery has also been tried. Still, patient immobilization is required until clot formation stabilizes the site. Other problems, such as distal embolization of the collagen, rebleeding, and the need for external pressure to achieve hemostatis, also persist.

As another example, devices that surgically suture the puncture site percutaneously have also been used. The devices require the practice of fine surgical skills to place needles at a precise distance from the edges of the puncture orifice and to form an array of suture knots, which are tightened and pushed from the skin surface to the artery wall with a knot pusher, resulting in puncture edge apposition.

There remains a need for fast and straightforward mechanical and chemical systems and methods to close vascular puncture sites and to accelerate the patient's return to ambulatory status without pain and prolonged immobilization.

There also remains a demand for biomaterials that improve the technique, cost efficiency, and efficacy of these and other therapeutic indications.

SUMMARY OF THE INVENTION

The invention provides a method that mixes a first component, a second component, and a buffer material. The first component includes an electrophilic polymer material comprising poly(ethylene glycol) having a functionality of at least three. The second component includes a nucleophilic material comprising a natural or synthetic protein at a concentration of about 25% or less that, when mixed with the first component within a reaction pH range, cross-links with the first component to form a non-liquid, three-dimensional barrier. The buffer material includes tris-hydroxymethylaminomethane having a pH within the reaction pH range. The method applies the mixture to adhere to a tissue region.

Features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

I. Overview

Figure 1:
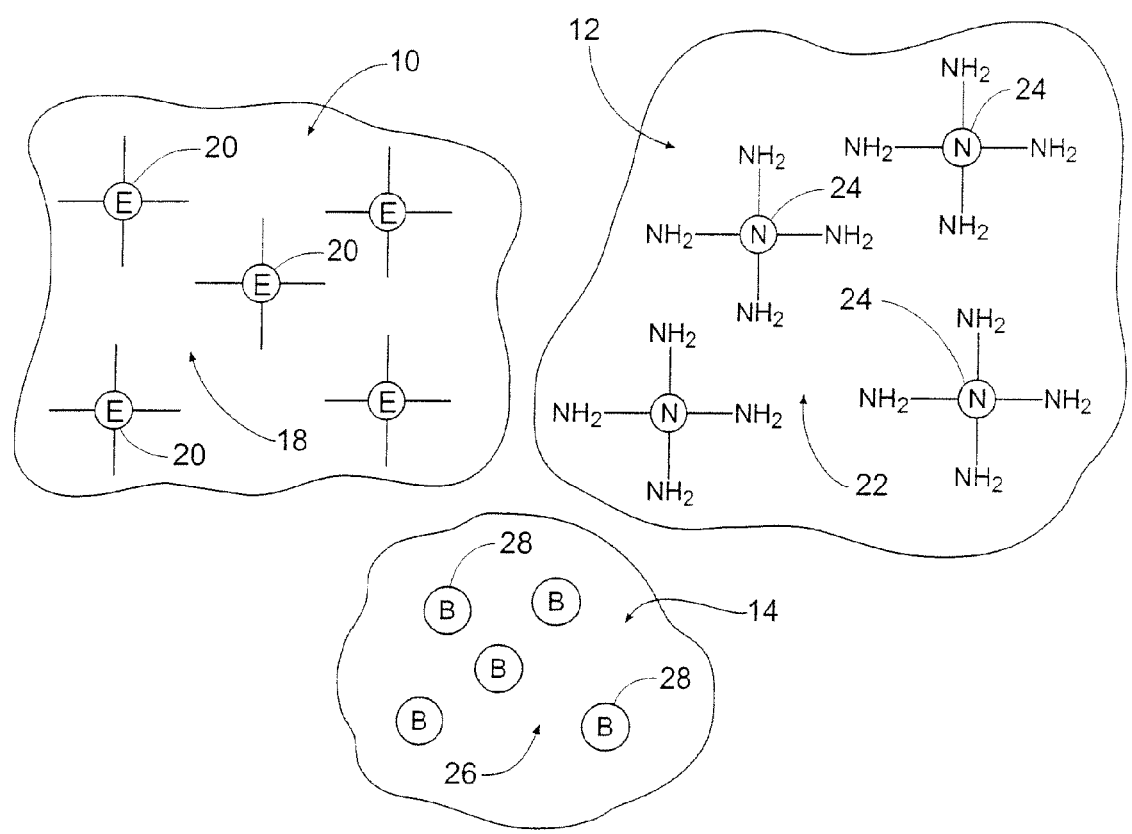
FIG. 1 is a diagrammatic view of the basic formative components which, when mixed in a liquid state, cross-link to form a solid biocompatible material composition that is well suited for closing a vascular puncture site.
Figure 2:
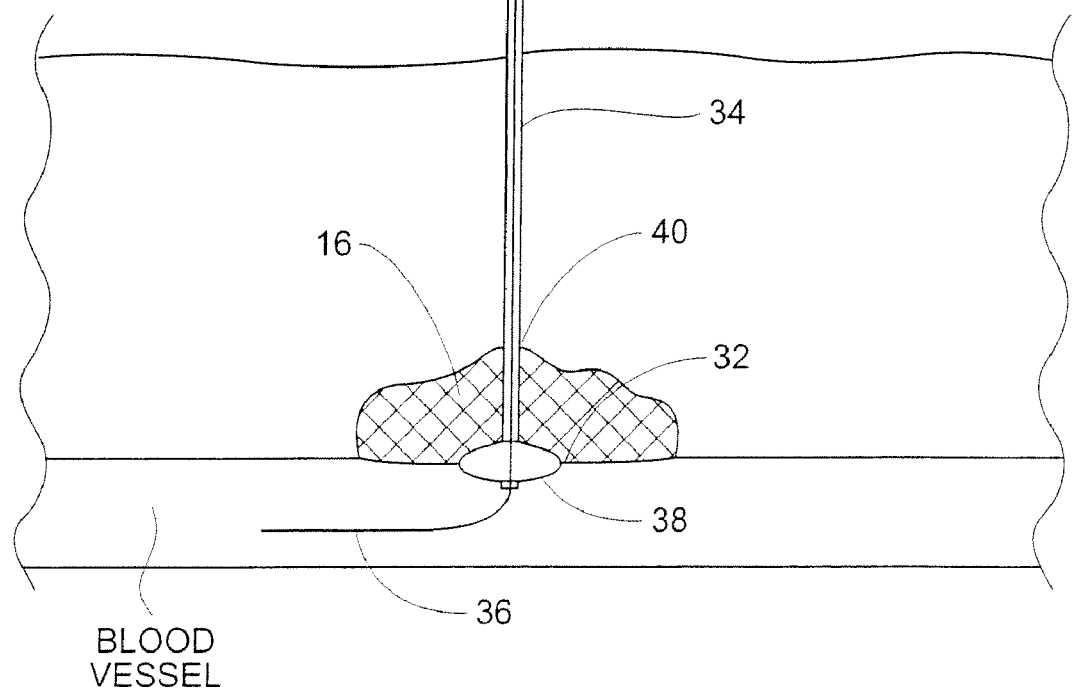
FIG. 2 is a schematic view of a system for delivering the basic formative components, while in a liquid state, to a vascular puncture site.
Figure 3:
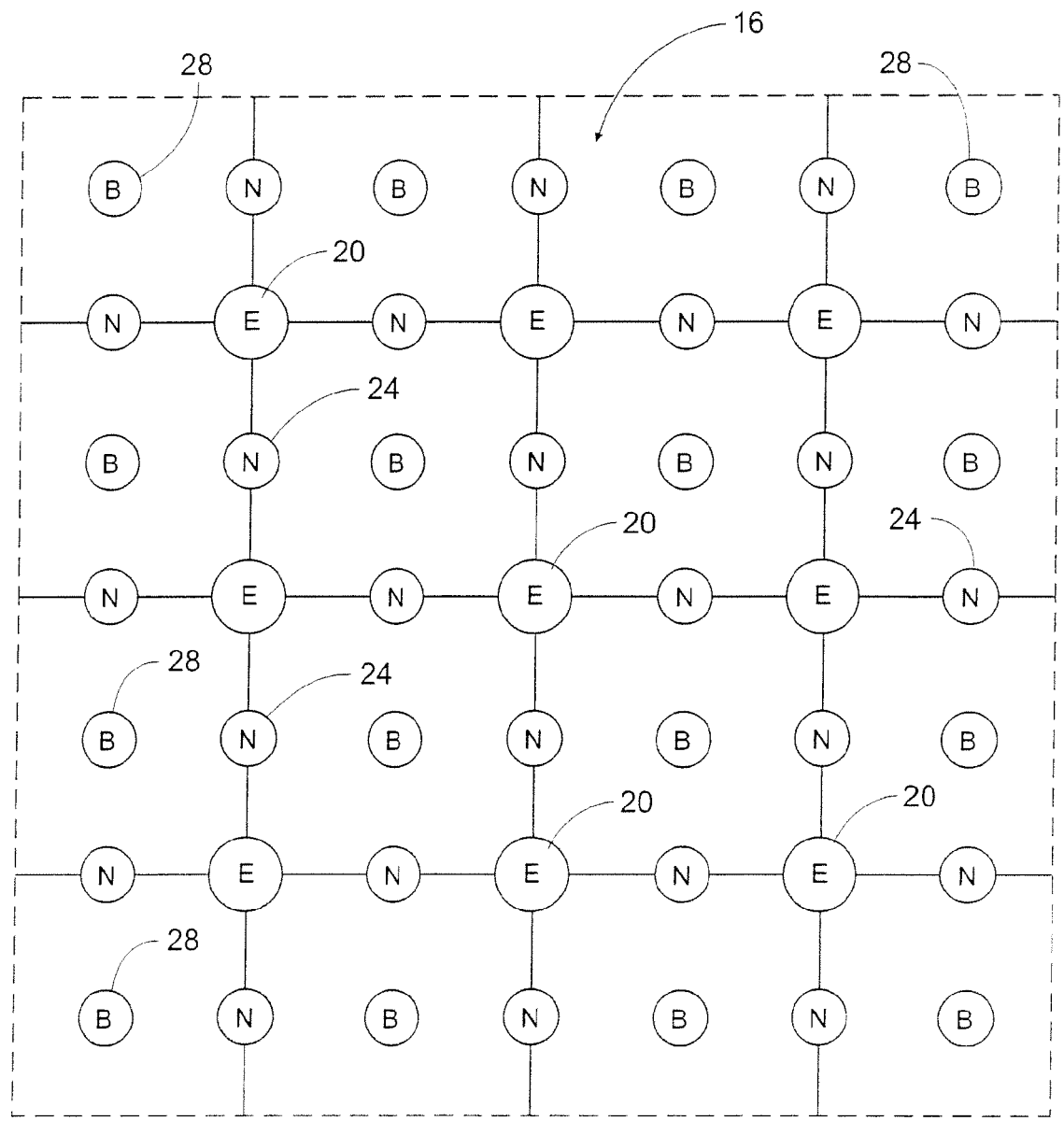
FIG. 3 is a diagrammatic view of the resulting non-liquid, three-dimensional composition that forms after the formative components, shown in FIG. 1, cross-link to transform from a liquid state, to a semi-solid (gel) state, and then to a biocompatible solid state, which closes the vascular puncture site.

FIG. 1 diagrammatically shows the basic formative components 10, 12, and 14 of a solid biocompatible material composition 16, which is shown in FIGS. 2 and 3 after the components 10, 12, and 14 have been mixed. The composition 16 is well suited for closing a vascular puncture site, e.g., following a vascular access procedure. The formative components 10, 12, and 14 can be mixed in a liquid state while being delivered through a transcutaneous catheter 30 to the puncture site 32 (see FIG. 2). Upon mixing, the formative components 10, 12, and 14 react to transform in situ from the liquid state, to a semi-solid (gel) state, and then to the biocompatible solid state, in a process called "gelation." In the solid state, the composition 16 takes the form of a non-liquid, three-dimensional network (as diagrammatically shown in FIG. 3).

The solid material composition 16 exhibits desired mechanical properties. These properties include adhesive strength (adhering it to adjacent tissue), cohesive strength (forming a mechanical barrier that is resistant to blood pressure and blood seepage), and elasticity (accommodating the normal stresses and strains of everyday activity). These properties, as well as the relative rapid rate of gelation that can be achieved, serve to provide a fast and effective closure to the vascular puncture site.

The solid material composition 16 is also capable of transforming over time by physiological mechanisms from the solid state to a biocompatible liquid state, which can be cleared by the body, in a process called "degradation."

The time period that begins when the components 10, 12, and 14 have been mixed and ends when the composition has reached the semi-solid (gel) state will be called the "gelation time." When in this state, the composition possesses sufficient cohesive and adhesive strength to impede blood flow, but still retains a self-sealing property, possessing the capacity to close in upon and seal the tract left by the catheter in the composition when the physician removes the catheter. For sealing a vascular puncture site, the composition 16 preferably possesses a gelation time that is in the range of fifteen to sixty seconds. A gelation time in the range of fifteen to thirty seconds is most preferred. This period allows the components 10, 12, and 14 forming the composition 16 to flow first in a liquid state, and then in the semi-solid (gel) state, outward along the axis of the blood vessel. The flow of components during gelation fills surface irregularities in the tissue region of the vascular puncture site 32, before solidification occurs. A gelation time period of between 10 and 40 seconds also falls well within the time period a physician typically needs to manipulate and remove the catheter 30 after delivery of the components to the puncture site 32. With an experienced physician, the catheter manipulation and removal time period can be as quick as 10 to 40 seconds, but it can extend, due to circumstances, upwards to 2 minutes. With a gelation time falling within the preferred range, the formation of the material composition 16 does not require a physician to "watch the clock," but rather attend only to the normal tasks of injecting the material and then manipulating and removing the catheter 30. With a gelation time falling within the preferred range, it has been discovered that, if the catheter is removed in 15 seconds to 2 minutes following initial mixing, the composition 16 has reached a physical state capable of performing its intended function, while still accommodating a sealed withdrawal of the catheter. Desirably, after removal of the catheter, the physician applies localized and temporary finger pressure to the skin surface above the composition for a period of about 5 minutes, to aid in the closure of the catheter tract in the composition, as the composition reaches its solid state.

The composition 16 preferably possesses sufficient adhesive strength to prevent dislodging from the arteriotomy, once formed. The composition 16 also has sufficient cohesive strength to prevent rupture under arterial pressure, i.e., up to about 200 mm Hg. The composition 16 seals the arteriotomy for up to 15 days post-application before loss of mechanical properties through degradation, and degrades by 30 to 90 days post-application.

II. The Formative Components

Figure 5:
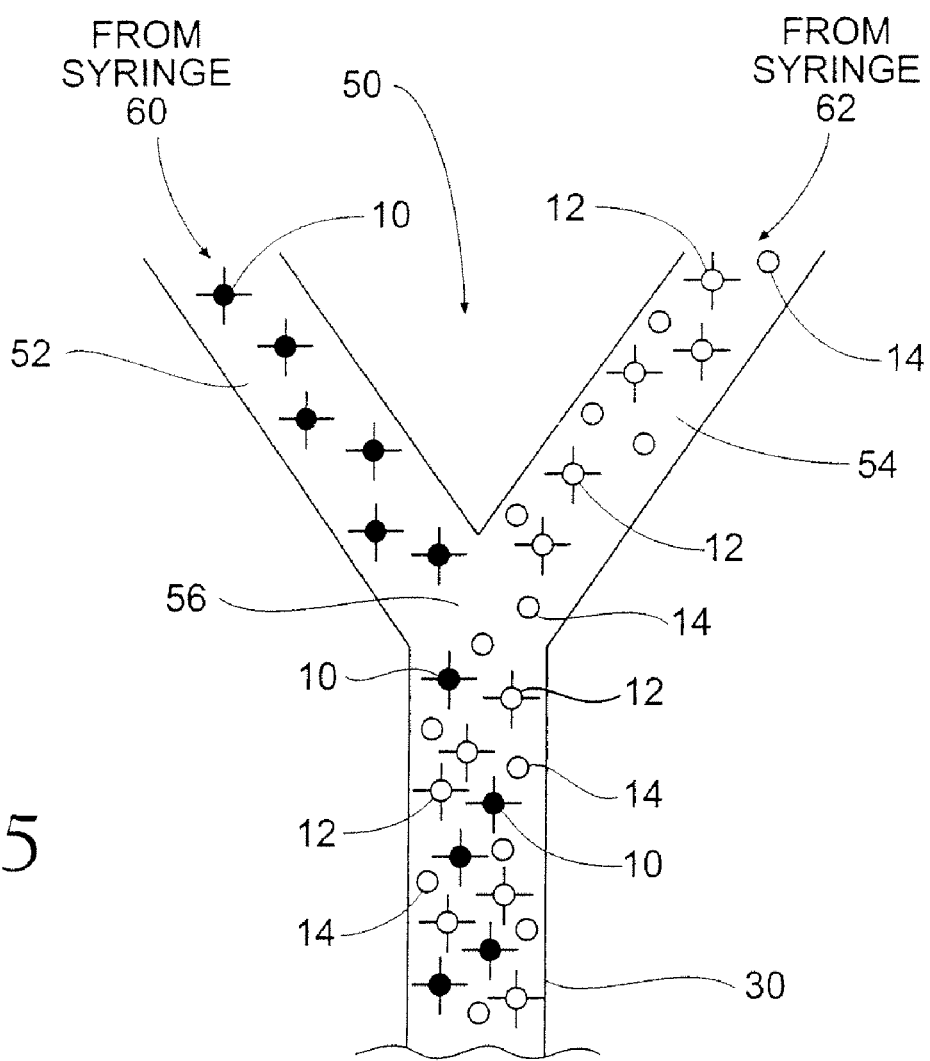
FIG. 5 is a diagrammatic view showing operation of the catheter device shown in FIG. 4 to mix the basic formative components shown in FIG. 1, to deliver the components to a vascular puncture site, where the resulting cross-linking reaction affects closure to the vascular puncture site.
Figure 5:
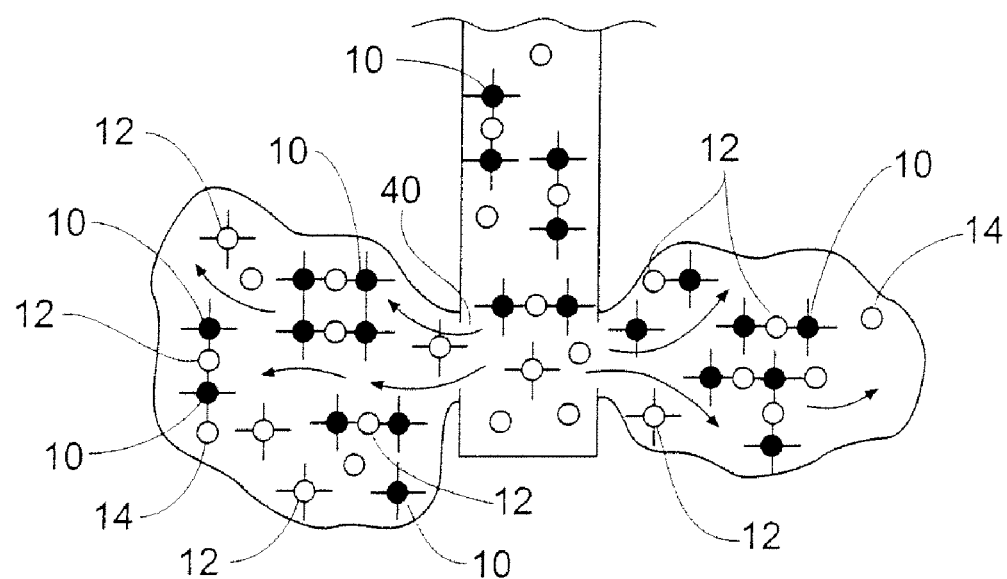

The formative component 10 (see FIG. 1) comprises a solution 18 containing an electrophilic (electrode withdrawing) material 20 having a functionality of at least three. The formative component 12 comprises a solution 22 containing a nucleophilic (electron donator) material 24. When mixed under proper reaction conditions, the electrophilic material 20 and nucleophilic material 24 react, by cross-linking with each other (as FIG. 5 diagrammatically shows). The cross-linking of the materials 20 and 24 form the composition 16, which is diagrammatically shown in FIG. 3. The composition 16 physically forms a mechanical barrier, which can also be characterized as a hydrogel.

The formative component 14 comprises a solution 26 containing a buffer material 28. The type and concentration of the buffer material controls the pH of the components 10 and 12, when brought into contact for mixing. The buffer material 14 desirably establishes an initial pH in numeric terms, as well regulates change of the pH over time (a characteristic that will be called the "buffering capacity").

The gelation time (which indicates the rate at which the cross-linking reaction occurs) is controlled, inter alia, by the reaction pH, which the buffer component 14 establishes. The reaction pH controls the reactivity of nucleophilic groups in the second component 12, which react with the electrophilic groups in the first component 10. Generally speaking, the higher the reaction pH is, the larger is the fraction of nucleophilic groups available for reaction with the electrophilic groups, and vice versa.

To achieve a relatively rapid gelation time, a relatively high initial reaction pH (which, for the illustrated components, is above 8) is desirable at the time initial mixing of the components 10, 12, and 14 occurs. On the other hand, by the time the mixture is brought into contact with body tissue at the vascular puncture site, it is desirable that mixture possess a more physiologically tolerated pH level (approximately 7.4).

However, it has been discovered that, if the initial reaction pH is too high (which, for the illustrated components, is believed to be a pH approaching about 9), the gelation time may be too rapid to consistently accommodate the time period a physician typically requires to remove the catheter, particularly if the time period approaches the two minute mark. In this instance, by the two minute mark, substantial solidification of the composition can occur, and the composition can lack the cross-linking capacity to close in about the catheter tract left in the composition upon removal of the catheter. Under these circumstances, blood leakage and hematoma formation can result after removal of the catheter.

Achieving and sustaining a reaction pH to meet a targeted gelation time is therefor a critical criteria. It has been discovered that, by purposeful selection of the components 10, 12, and 14, (i) an initially high reaction pH can be established that is conducive to rapid gelation, before contact with body tissue occurs, and (ii) the reaction pH can be lowered as gelation progresses, as the mixture is delivered through the catheter into contact with body tissue at the vascular puncture site. At the same time, by purposeful selection of the components 10, 12, and 14, the rate at which the pH is lowered during delivery can be mediated, so that gelation is sustained at a rate that meets the gelation time requirements to achieve the desired in situ formation of the composition 16, one that also possesses sufficient cross-linking capacity to close about the catheter tract following removal of the catheter 30 after a time period a physician typically needs to perform this task.

In this context, the first component 10 desirably takes the form of a solution 18 of an electrophilic derivative of a hydrophilic polymer (which will also sometimes be referred generically as a "polymer solution."). The second component 12 desirably takes the form of a solution of a material with nucleophilic groups (e.g., amines or thiols) (which will also sometimes be referred generically as a "protein solution.").

The nucleophilic groups of the solution component 12 are also naturally present in the physiologic environment in which the composition 16 forms. Thus, the same cross-linking reaction that occurs between the electrophlic groups of the polymer solution and the nucleophilic groups of the protein solution—building interior cohesive strength to the composition 16—will also occur between the electrophlic groups of the polymer solution and the nucleophilic groups of body tissue—giving tissue adhesive strength to the composition 16 at the vessel puncture site.

Furthermore, as the components 10 and 12 aggressively cross-link in a favorably high reaction pH environment, their cross-linking forms a non-toxic, acidic leaving group. Thus, as the gelation reaction proceeds at a high rate in a favorable high pH environment, the acidic leaving groups that are foamed will self-promote a decrease in the reaction pH, so that the pH of the mixture can be lowered to a more physiologically tolerated pH level by the time it makes contact with body tissue. Once contact with body tissue occurs, the reaction pH will continue to be mediated by the surrounding pH (7.3 to 7.4) of the tissue region.

The rate of gelation will, of course, slow as the pH drops. To sustain an acceptable rate of gelation as the reaction environment becomes more acidic, the type and concentration of the buffer material 28 are selected to provide a desired buffering capacity. The greater the buffering capacity is, the greater is the ability of the buffering material 28 to absorb acidic groups as they form and mediate the rate at which the pH (and thus rate of gelation) drops, both before and after entry into the body.

Further details of the most preferred, representative forms of the components follow.

A. The Electrophilic Component

In its most preferred form, the electrophilic (electrode withdrawing) material 20 comprises a hydrophilic, biocompatible polymer that is electrophilically derivatized with a functionality of at least three. Examples include poly(ethylene glycol), poly(ethylene oxide), poly(vinyl alcohol), poly(vinylpyrrolidinone), poly(ethyloxazoline), and poly(ethylene glycol)-co-poly(propylene glycol) block copolymers.

As used herein, a polymer meeting the above criteria is one that begins with a multiple arm core (e.g., pentaerythritol) and not a bifunctional starting material, and which is synthesized to a desired molecular weight (by derivatizing the end groups), such that polymers with functional groups greater than or equal to three constitute (according to gel permeation chromatography—GPC) at least 50% or more of the polymer blend.

The material 20 is not restricted to synthetic polymers, as polysaccharides, carbohydrates, and proteins could be electrophilically derivatized with a functionality of at least three. In addition, hybrid proteins with one or more substitutions, deletions, or additions in the primary structure may be used as the material 20. In this arrangement, the protein's primary structure is not restricted to those found in nature, as an amino acid sequence can be synthetically designed to achieve a particular structure and/or function and then incorporated into the material. The protein of the polymer material 20 can be recombinantly produced or collected from naturally occurring sources.

Preferably, the polymer material 20 is comprised of poly(ethylene glycol) (PEG) with a molecular weight preferably between 9,000 and 12,000, and most preferably 10,500±1500. PEG has been demonstrated to be biocompatible and non-toxic in a variety of physiological applications. The preferred concentrations of the polymer are 5% to 35% w/w, more preferably 5% to 20% w/w. The polymer can be dissolved in a variety of solutions, but sterile water is preferred.

The most preferred polymer material 20 can be generally expressed as compounds of the formula:

Where:
DCR is a degradation control region.
CG is a cross-linking group.
$n \geq 3$ The electrophilic CG is responsible for the cross-linking of the preferred nucleophilic material 24, as well as binding the composition 16 to the like material in the surrounding tissue, as will be described later. The CG can be selected to selectively react with thiols, selectively react with amines, or react with thiols and amines. CG's that are selective to thiols include vinyl sulfone, N-ethyl maleimide, iodoacetamide, and orthopyridyl disulfide. CG's that are selective to amines include aldehydes. Non-selective electrophilic groups include active esters, epoxides, oxycarbonylimidazole, nitrophenyl carbonates, tresylate, mesylate, tosylate, and isocyanate. The preferred CG's are active esters, more preferred, an ester of N-hydroxysuccinimide. The active esters are preferred since they react rapidly with nucleophilic groups and have a non-toxic leaving group, e.g., hydroxysuccinimide.

The concentration of the CG in the polymer material 20 can be used to control the rate of gelation. However, changes in this concentration typically also result in changes in the desired mechanical properties of the hydrogel.

The rate of degradation is controlled by the degradation control region (DCR), the concentration of the CG's in the polymer solution, and the concentration of the nucleophilic groups in the protein solution. Changes in these concentrations also typically result in changes in the mechanical properties of the hydrogel, as well as the rate of degradation.

The rate of degradation (which desirably occurs in about 30 days) is best controlled by the selection of the chemical moiety in the degradation control region, DCR. If degradation is not desired, a DCR can be selected to prevent biodegradation or the material can be created without a DCR. However, if degradation is desired, a hydrolytically or enzymatically degradable DCR can be selected. Examples of hydrolytically degradable moieties include saturated di-acids, unsaturated di-acids, poly(glycolic acid), poly(DL-lactic acid), poly(L-lactic acid), poly(.xi.-caprolactone), poly(.delta.-valerolactone), poly(.gamma.-butyrolactone), poly(amino acids), poly(anhydrides), poly(orthoesters), poly(orthocarbonates), and poly(phosphoesters), and derivatives thereof. A preferred hydrolytically degradable DCR is gluturate. Examples of enzymatically degradable DCR's include Leu-Gly-Pro-Ala (collagenase sensitive linkage, SEQ. I.D. NO. 1) and Gly-Pro-Lys (plasmin sensitive linkage). It should also be appreciated that the DCR could contain combinations of degradable groups, e.g. poly(glycolic acid) and di-acid.

While the preferred polymer is a multi-armed structure, a linear polymer with a functionality, or reactive groups per molecule, of at least three can also be used. The utility of a given PEG polymer significantly increases when the functionality is increased to be greater than or equal to three. The observed incremental increase in functionality occurs when the functionality is increased from two to three, and again when the functionality is increased from three to four. Further incremental increases are minimal when the functionality exceeds about four.

A preferred polymer may be purchased from Shearwater Polymers Inc. (Product Designation: PEG4SG, having a molecular weight range of between 9000 and 12,000) (which will be called the "Shearwater PEG"). Gel permeation chromotography of the Shearwater PEG reveals that (by molecular weight) 59.2% of the Shearwater PEG comprises 4-Arm-PEG polymer.

Alternatively, another preferred polymer may be purchased from SunBio Company ((PEG-SG)4, having a molecular weight of 10,500±1500) (which will be called the "SunBio PEG"). Gel permeation chromotography of the SunBio PEG reveals that (by molecular weight) 3.1% of the SunBio PEG comprises 3-Arm-PEG polymer and 90.7% of the SunBio PEG comprises 4-Arm-PEG polymer. When compared to the Shearwater PEG, it can be seen that the SunBio PEG contains a greater concentration of PEG polymers with a functionality equal to or greater than 3.

B. The Nucleophilic Component

In a most preferred embodiment, the nucleophilic material 24 includes non-immunogenic, hydrophilic proteins. Examples include serum, serum fractions, and solutions of albumin, gelatin, antibodies, fibrinogen, and serum proteins. In addition, water soluble derivatives of hydrophobic proteins can be used. Examples include solutions of collagen, elastin, chitosan, and hyaluronic acid. In addition, hybrid proteins with one or more substitutions, deletions, or additions in the primary structure may be used.

Furthermore, the primary protein structure need not be restricted to those found in nature. An amino acid sequence can be synthetically designed to achieve a particular structure and/or function and then incorporated into the nucleophilic material 24. The protein can be recombinantly produced or collected from naturally occurring sources.

The preferred protein solution is 25% human serum albumin, USP. Human serum albumin is preferred due to its biocompatibility and its ready availability.

The uses of PEG polymers with functionality of greater than three provides a surprising advantage when albumin is used as the nucleophilic material 24. When cross-linked with higher functionality PEG polymers, the concentration of albumin can be reduced to 25% and below. Past uses of difunctional PEG polymers require concentrations of albumin well above 25%, e.g. 35% to 45%. Use of lower concentrations of albumin result in superior tissue sealing properties with increased elasticity, a further desired result. Additionally, 25% human serum albumin, USP is commercially available from several sources, however higher concentrations of human serum albumin, USP are not commercially available. By using commercially available materials, the dialysis and ultrafiltration of the albumin solution, as disclosed in the prior art, is eliminated, significantly reducing the cost and complexity of the preparation of the albumin solution.

To minimize the liberation of heat during the cross-linking reaction, the concentration of the cross-linking groups of the fundamental polymer component is preferably kept less than 5% of the total mass of the reactive solution, and more preferably about 1% or less. The low concentration of the cross-linking group is also beneficial so that the amount of the leaving group is also minimized. In a typical clinical application, about 50 mg of a non-toxic leaving group is produced during the cross-linking reaction, a further desired result. In a preferred embodiment, the CG comprising an N-hydroxysuccinimide ester has demonstrated ability to participate in the cross-linking reaction with albumin without eliciting adverse immune responses in humans.

C. The Buffer Component

In the most preferred embodiment, a PEG reactive ester reacts with the amino groups of the albumin and other tissue proteins, with the release of N-hydroxysuccinimide and the formation of a link between the PEG and the protein. When there are multiple reactive ester groups per PEG molecule, and each protein has many reactive groups, a network of links form, binding all the albumin molecules to each other and to adjacent tissue proteins.

This reaction with protein amino groups is not the only reaction that the PEG reactive ester can undergo. It can also react with water (i.e., hydrolyze), thereby losing its ability to react with protein. For this reason, the PEG reactive ester must be stored dry before use and dissolved under conditions where it does not hydrolyze rapidly. The storage container for the PEG material desirably is evacuated by use of a vacuum, and the PEG material is stored therein under an inert gas, such as Argon or Nitrogen. Another method of packaging the PEG material is to lyophilize the PEG material and store it under vacuum, or under an inert gas, such as Argon or Nitrogen. Lyophilization provides the benefits of long term storage and product stability, as well as allows rapid dissolution of the PEG material in water.

The conditions that speed up hydrolysis tend to parallel those that speed up the reaction with protein; namely, increased temperature; increased concentration; and increased pH (i.e., increased alkali). In the illustrated embodiment, temperature cannot be easily varied, so varying the concentrations and the pH are the primary methods of control.

It is the purpose of the buffer material 28 to establish an initial pH to achieve a desired gelation time, and to sustain the pH as added acid is produced by the release of N-hydroxysuccinimide during cross linking and hydrolysis.

pH is the special scale of measurement established to define the concentration in water of acid (H+) or alkali (OH−) (which, strictly speaking, indicates hydrogen ion activity). In the pH scale, solutions of acid (H+) in water have a low pH, neutrality is around pH 7, and solutions of base (OH−) in water have a high pH. The pH scale is logarithmic. A change of one pH unit (e.g., from pH 9 to pH 10) corresponds to a ten-fold change in concentration (i.e., hydrogen ion activity). Thus, reactions which are increased by alkali, such as hydrolysis of PEG reactive ester, are expected to increase in rate by a factor of ten for each unit increase in pH.

The buffer material 28 is a mixture of molecules, added to the albumin, that can moderate pH changes by reacting reversibly with added acid (H+) or base (OH−). The pH moderating effect can be measured by titration, i.e., by adding increasing amounts of H+ or OH− to the buffer material, measuring the pH at each step, and comparing the pH changes to that of a similar solution without the buffer.

Different buffers exert a maximum pH moderating effect (i.e., the least change in pH with added H+ or OH−) at different pH's. The pH at which a given buffer exerts its maximum pH moderating effect is called its pK.

Even when the pH matches the pK for a given buffer, added acid or base will produce some change in pH. As the pH changes from the pK value, the moderating effect of the buffer decreases progressively (e.g., 67% less at +/−1 pH unit from pK, and 90% less at +/−1.6 pH unit from pK). The moderating effect is also proportional to the buffer concentration. Thus, increasing the buffer concentration increases the ability to moderate pH changes.

The overall buffering effect at any pH is the sum of all buffering species present, and has also been earlier called the buffering capacity. The higher the buffering capacity, the more acid or base must be added to produce a given pH change. Stated differently, the higher the buffering capacity, the longer a given buffer is able to sustain a targeted pH range as acid or base is being added to change the pH.

Albumin itself contains amino, carboxyl, and other groups, which can reversibly react with acid and base. That is, albumin itself is a buffer. Also, due to the many different buffering groups that albumin possesses, albumin (e.g., Plasbumin) can buffer over a relatively broad pH range, from below pH 6 to over pH 10. However, it has been discovered that albumin lacks the buffering capacity to, by itself, counterbalance the additional acid (H+) that is produced as a result of hydrolysis and the PEG-albumin cross-linking, given the PEG concentrations required to meet the therapeutic objectives for the composition. Thus, in the preferred embodiment, a buffer material 28 must be added to the albumin to provide the required buffering capacity.

The buffer material 28 must meet several criteria. The buffer material must be (1) non-toxic, (2) biocompatible, (3) possess a pK capable of buffering in the pH range where the desirable gelation time exists, and (4) must not interfere with the reaction of protein with the selected PEG reactive ester. Amine-containing buffers do not meet criteria (4).

To meet criteria (3), the buffer material 28 should have a buffering capacity at the desired cross-linking pH (i.e., as indicated by its pK) that is high enough to counterbalance the additional acid (H+) produced as a result of the cross-linking reaction and hydrolysis, i.e., to keep the pH high enough to achieve the desired gelation time.

It has been discovered, through bench testing, that when cross-linking the Shearwater PEG and SunBio PEG with albumin (Plasbumin), a range of gelation times between an acceptable moderate time (about 30 seconds) to a rapid time (about 2 seconds) can be achieved by establishing a pH range from about 8 (the moderate times) to about 10 (the rapid times). Ascertaining the cross-linking pH range aids in the selection of buffer materials having pK's that can provide the requisite buffering capacity within the pH range.

Phosphate, tris-hydroxymethylaminomethane (Tris), and carbonate are all non-toxic, biocompatible buffers, thereby meeting criteria (1) and (2). Phosphate has a pK of about 7, which provides increased buffering capacity to albumin at pH's up to about 8.5. Tris has a pK of about 8, which provides increased buffering capacity to albumin at pH's up to about 9.5. Addition of Tris to albumin (Plasbumin) at a concentration of 60 mM approximately doubles the buffering capacity of the albumin at a pH near 9. Carbonate has a pK of about 10, and provides increased buffering capacity to albumin in the higher pH ranges. Depending upon the gellation time that is targeted, formulations of Tris, carbonate, and albumin can be used for the buffer material 24.

Example 1

Sodium Carbonate/Sodium Phosphate Buffer Formulations

Albumin (Human 25%, Plasbumin®-25 manufactured by Bayer Corporation) was buffered using differing amounts of Sodium Carbonate Monohydrate ($Na_2CO_3H_2O$)(FW 124.00) ("Carbonate Buffer") and Sodium Phosphate Monobasic Monohydrate ($NaH_2PO_4H_2O$)(FW 137.99) ("Phosphate Buffer"). The buffered albumin formulations (2 cc) were mixed with 2 cc of the Shearwater PEG (0.45 g of PEG suspended in 2.2 cc of water), to provide 17% w/w PEG solids. The components were mixed by using the catheter device as generally shown in FIG. 2 (and as will be described in greater detail later). Upon mixing, the components were deposited in a test dish. The pH of the buffered albumin formulation (albumin plus buffer material) and the gelation time (as described above) and were recorded.

Table 1 summarizes the results.

TABLE 1

| Albumin (Human 25%) (ml) | Carbonate Buffer (grams) | Phosphate Buffer (grams) | pH | Device (Outside Diameter) | Gelling Time (Seconds) |
|---|---|---|---|---|---|
| 50 | 0.375 | 0.275 | 8.0 | 8 Fr | 70 |
| 50 | 0.375 | 0.275 | 8.0 | 5.5 Fr | 70 |
| 50 | 0.60 | 0.275 | 9.0 | 8 Fr | 30 |
| 50 | 0.95 | 0.275 | 9.5 | 8 Fr | 15 |

Table 1 shows that increasing the amount of Carbonate Buffer (pK 10) increases the pH and likewise reduces the gelation time. However, gelation times falling within the desired range required higher, less desirable pH's.

Example 2

Carbonate Buffer/Tris Buffer Formulations

Albumin (Human 25%, Plasbumin®-25 manufactured by Bayer Corporation) was buffered using Sodium Carbonate Anhydrous ($Na_2CO_3$)(FW 106.0) ("Carbonate Buffer") mixed with Tris-hydroxymethylaminomethane ($C_4H_{11}NO_3$) (FW 121.1) ("Tris Buffer"). The buffered albumin formulations (2 cc) were mixed with 2 cc of the Shearwater PEG (0.45 g of PEG suspended in 2.2 cc of water), to provide 17. % w/w PEG solids, in the same manner as Example 1. The pH of the buffered albumin formulation (albumin plus buffer material) and the gelation time (as described above) and were recorded.

Table 2 summarizes the results.

TABLE 2

| Albumin (Human 25%) (ml) | Carbonate Buffer (grams) | Tris Buffer (grams) | pH | Device (Outside Diameter) | Gelling Time (Seconds) |
|---|---|---|---|---|---|
| 20 | 0.137 | 0.145 | 9.0 | 8 Fr | 15-16 |
| 20 | 0.137 | 0.145 | 9.0 | 8 Fr | 15-16 |

Table 2 shows faster gelation times, compared to the gelation times in Table 1, despite the presence of less Carbonate Buffer (pK 10). The more rapid gelling times are due to the increased buffering capacity that the Tris Buffer (pK 8) provides in the pH range 7 to 9. In comparison, the Carbonate Buffer has little buffer capacity in the pH 7 to 9 range, being more effective at higher pH's. The higher pH levels (above about pH 9) are not desirable, as the composition is not quickly neutralized by blood contact to terminate gelation (at about pH 7.4), should leakage of the composition into a blood path occur. Better buffering capacity that the Tris Buffer provides in the pH 7 to 9 range keeps the pH from dropping as quickly, which, in turns, consistently leads to a gelation time falling within the desired range and at lower pH levels. The lower pH levels (below about pH 9) are desirable because the composition is more quickly neutralized by blood contact (at about pH 7.4), so that the potential for gellation within the blood path is minimized.

Example 3

Carbonate Buffer/Tris Buffer Formulations

Albumin (Human 25%, Plasbumin®-25 manufactured by Bayer Corporation) was buffered using Sodium Carbonate Anhydrous ($Na_2CO_3$)(FW 106.0) ("Carbonate Buffer") mixed with Tris-hydroxymethylaminomethane ($C_4H_{11}NO_3$) (FW 121.1) ("Tris Buffer"). The buffered albumin formulations (2 cc) were mixed with 2 cc of the SunBio PEG (0.45 g of PEG suspended in 2.2 cc of water), to provide 17% w/w PEG solids. The components were mixed in the manner described in Example 1. The pH of the buffered albumin formulation (albumin plus buffer material) and the gelation time (as described above) and were recorded.

Table 3 summarizes the results.

TABLE 3

| Albumin (Human 25%) (ml) | Carbonate Buffer (grams) | Tris Buffer (grams) | pH | Device (Outside Diameter) | Gelling Time (Seconds) |
|---|---|---|---|---|---|
| 20 | 0 | 0.217 | 8.3 | 7 Fr | 11 |
| 20 | 0 | 0.290 | 8.5 | 7 Fr | 7-8 |
| 20 | 0.075 | 0.145 | 8.7 | 7 Fr | 5-6 |
| 20 | 0.138 | 0.145 | 9.0 | 7 Fr | 2-3 |

Table 3 shows even faster gelation times, compared to the gelation times in Tables 1 and 2, at lower pH's. This is believed due to the larger concentration of multiple functionality PEG in the SunBio PEG, as well as the enhanced buffering capacity that the Tris Buffer (pK 8) provides in the lower pH range (7 to 9). It is also believed that the gelation time will also vary, given the same composition, according to the size and configuration of the delivery device. The addition of Carbonate Buffer (in the pH 8.7 and pH 9 compositions) leads to a further decrease in gelation time, at an increased pH.

Tests of pH 8.3 and pH 8.5 compositions in Table 3 have demonstrated that both composition are successful in sealing femoral puncture sites in sheep in 25 to 40 seconds. The tests also show that either composition possesses sufficient cross-linking capacity to close about the catheter tract following removal of the catheter upwards to two minutes after delivery of the material. Both compositions thereby readily accommodate variations in procedure time.

Tests of pH 8.7 composition in Table 3 have also demonstrated that the composition is successful in sealing femoral puncture sites in sheep in 25 to 40 seconds. The tests also show that, due to the more rapid gelation time, the composition does not possesses sufficient cross-linking capacity to consistently close about the catheter tract following removal of the catheter two minutes after delivery of the material. In this respect, the pH 8.7 composition, despite its faster gelation time, is not as accommodating to changes in procedure time as the pH 8.3 and pH 8.5 compositions, described above. For these reasons, the most preferred range for vessel puncture sealing is between pH 8.3 and pH 8.5.

II. Delivering the Formative Components to Create the Composition to Close Vascular Puncture Sites Generally speaking, there are four stages in creating the composition 16 to close a given vascular puncture site. These stages are: (1) the introduction stage; (2) the localized compression stage; (3) the hemostasis stage; and (4) the degradation stage.

The phase of the composition 16 differs in each stage, as different physical and physiological events unfold. These different composition phases are, respectively: (1) the liquid phase; (2) the semi-solid (gel) phase; (3) the solid phase; and (4) the re-absorption phase.

A. The Introduction Stage

The Composition Liquid Phase

In the first stage, the physician introduces the catheter 30 through a tissue track 34 to the site of the vascular puncture 32.

Typically, the catheter 30 is introduced along a guide wire 36 partially into the blood vessel (see FIG. 2). The guide wire 36 will have been previously introduced subcutaneously, through a wall of the blood vessel, to guide passage of a desired therapeutic or diagnostic instrument into the blood vessel, e.g., to perform coronary angioplasty. After performing the intended procedure, the therapeutic or diagnostic instrument is withdrawn, leaving the guide wire 36. The catheter 30 is introduced along the guide wire 36 to the puncture site 32. For reasons that will be explained in greater detail later, the diameter of the catheter 30 is preferably sized to seal, but not enlarge, the tissue track 34.

Figure 4:
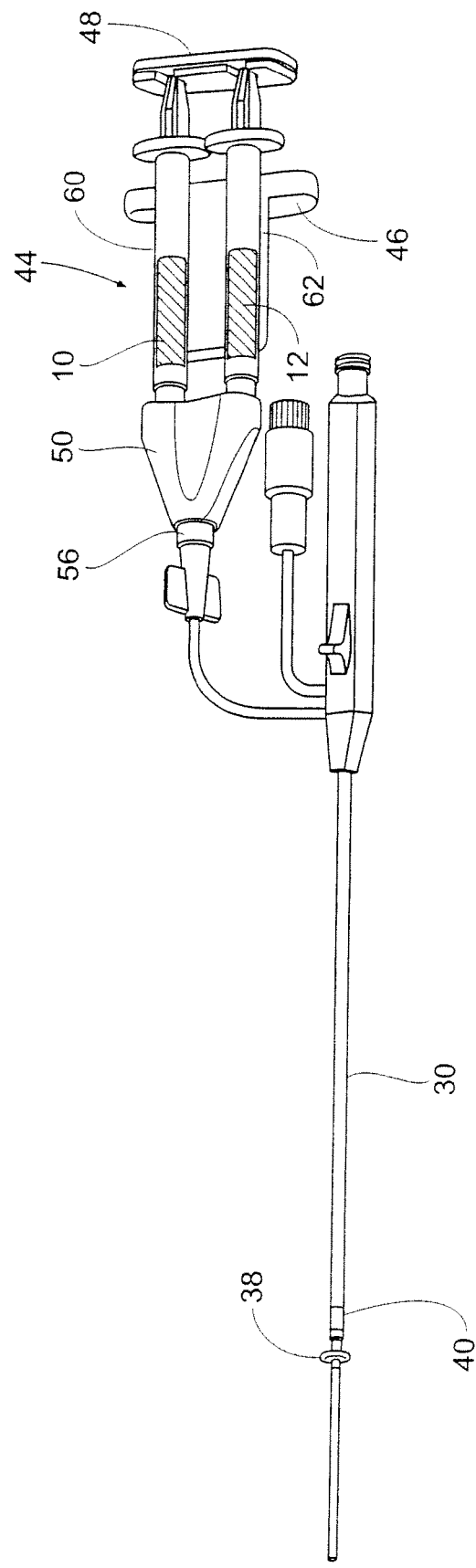
FIG. 4 is a perspective view of a catheter device that, when used in the manner shown in FIG. 2, delivers the basic formative components, while in a liquid state, to a vascular puncture site.

In the illustrated embodiment (see FIGS. 2 and 4), the distal end of the catheter 30 carries a balloon 38. When the balloon 38 is expanded within the blood vessel (as FIG. 2 shows), back pressure on the catheter 30 serves to locate (by tactile pressure) the distal nozzles 40 outside the puncture site 32 (see FIG. 4). The composition 16 is introduced through the nozzles 40.

A suitable material introducer/mixing device 44 is coupled to the distal end of the catheter 30. The device 44 can take various forms. In the illustrated embodiment (see FIG. 4), the device 44 includes a syringe support 46, which receives, e.g., in a snap-fit, two dispensing syringes 60 and 62. The pistons of the syringes 60 and 62 can be joined by a syringe clip 48. The clip 48 mechanically links the syringe pistons together for common advancement inside their respective syringe barrels.

The device 44 also includes a joiner 50 that includes two interior channels 52 and 54 (see FIG. 5). One channel 52 communicates with the syringe 60, and the other channel 54 communicates with the syringe 62. The channels merge at a Y-junction 56 into a single outlet port.

The joiner 50 maintains the two fluids dispensed by the syringes 60 and 62 separately until they leave the joiner 50. The outlet port communicates with an interior lumen in the catheter 30, which extends to the nozzles 40.

The syringe 60 contains the electrophilic component 10 suspended in solution in sterile water, e.g., 17% w/w 4-arm poly(ethylene glycol) tetra-succinimidyl glutarate, MW 10,500±1500 in water for injection (most preferably, the SunBio PEG, as described in Example 3).

The syringe 62 carries the nucleophilic component 12 suspended in solution, along with the buffer component 14, e.g., 25% w/w human serum albumin, USP supplemented with the Tris Buffer as shown in Table 3. The pH 8.3 and pH 8.5 compositions in Table 3 are most preferred.

Operation of the device 44 expresses the components 10, 12, and 14, while in liquid form, from the syringes 60 and 62. As FIG. 5 shows, the liquid components 10, 12, and 14 begin to mix at the junction 56. Here, the initially high reaction pH is established, to begin the cross-linking reaction at a desired high rate. Mixing and attendant gelation continue, as the components 10, 12, and 14 proceed in response to pressure exerted by the device 44 down the catheter lumen toward the nozzles 40.

Concurrently, the formation of the acidic leaving groups serves to reduce the reaction pH. By the time the components 10, 12, and 14, which are still undergoing gelation, exit the nozzles 40, the reaction pH is approaching a more physiologically tolerated level. Once in contact with body tissue, the prevailing physiologic pH levels further mediate the reaction pH.

The gelating components 10, 12, and 14 flow out the nozzles 40 and into the surrounding tissue mass (as FIG. 5 shows). The catheter 30, which is sized to seal the tissue track 34, blocks substantial flow in a path up the tissue track 34.

Thus, the gelating components are directed in a flow radially away from the axis of the catheter 30 and along the axis of the vessel 42, as FIG. 5 shows.

The size of the catheter is selected according to the outside diameter of the introducer sheath used during the preceding therapeutic or diagnostic procedure, during which the arteriotomy was made. For example, a 6 Fr introducer sheath typically has an outside diameter of 7 Fr, so a 7 Fr diameter catheter is selected to seal the arteriotomy upon removal of the introducer sheath. The composition 16 is delivered in a liquid state adjacent to the arteriotomy, while the catheter 30 prevents the liquid from filling the tissue track. This feature ensures that the material composition 16 remains at the arteriotomy for maximum efficacy. The incoming flow, directed in this manner, creates a tissue space about the puncture site along the axis of the vessel. The gelating components fill this space.

In the gelation process, the electrophilic component 10 and the nucleophilic component 12 cross-link, and the developing composition 16 gains cohesive strength to close the puncture site. The electrophilic component 10 also begins to cross-link with nucleophilic groups on the surrounding tissue mass. Adhesive strength forms, which begins to adhere the developing composition 16 to the surrounding tissue mass.

During the gelation period, before internal cohesive and tissue adhesive strengths fully develop, a portion of the gelating components 10, 12, 14 can enter the blood vessel 42 through the puncture site 32. Upon entering the blood stream, the gelating components will immediately experience physical dilution. The dilution expands the distance between the electrophilic component 10 and the nucleophilic component 12, making cross-linking difficult. In addition, the diluted components now experience an environment having a pH (7.3 to 7.4) lower than the an effective reactive pH for cross-linking (which is above 8). As a result, incidence of cross-linking within the blood vessel, to form the hydrogel composition 16, is only a fraction of what it is outside the vessel, where gelation continues.

Furthermore, the diluted electrophilic component 10 will absorb nucleophilic proteins present in the blood. This reaction further reduces the reactivity of the electrophilic component 10. In blood, the diluted electrophilic component 10 is transformed into a biocompatible, non-reactive entity, which can be readily cleared by the kidneys and excreted. The diluted nucleophilic component 12 is a naturally occurring protein that is handled in normal ways by the body.

The Introduction Stage (The Composition Liquid Phase) preferably last about 5 to 30 seconds from the time the physician begins to mix the components 10, 12, and 14.

B. The Localized Compression Stage

The Semi-Solid Composition Phase

The second stage begins after the physician has delivered the entire prescribed volume of components 10, 12, and 14 to the tissue mass of the vessel puncture site and allowed the cross-linking of the components to progress to the point where a semi-solid gel occupies the formed tissue space.

Figure 6:
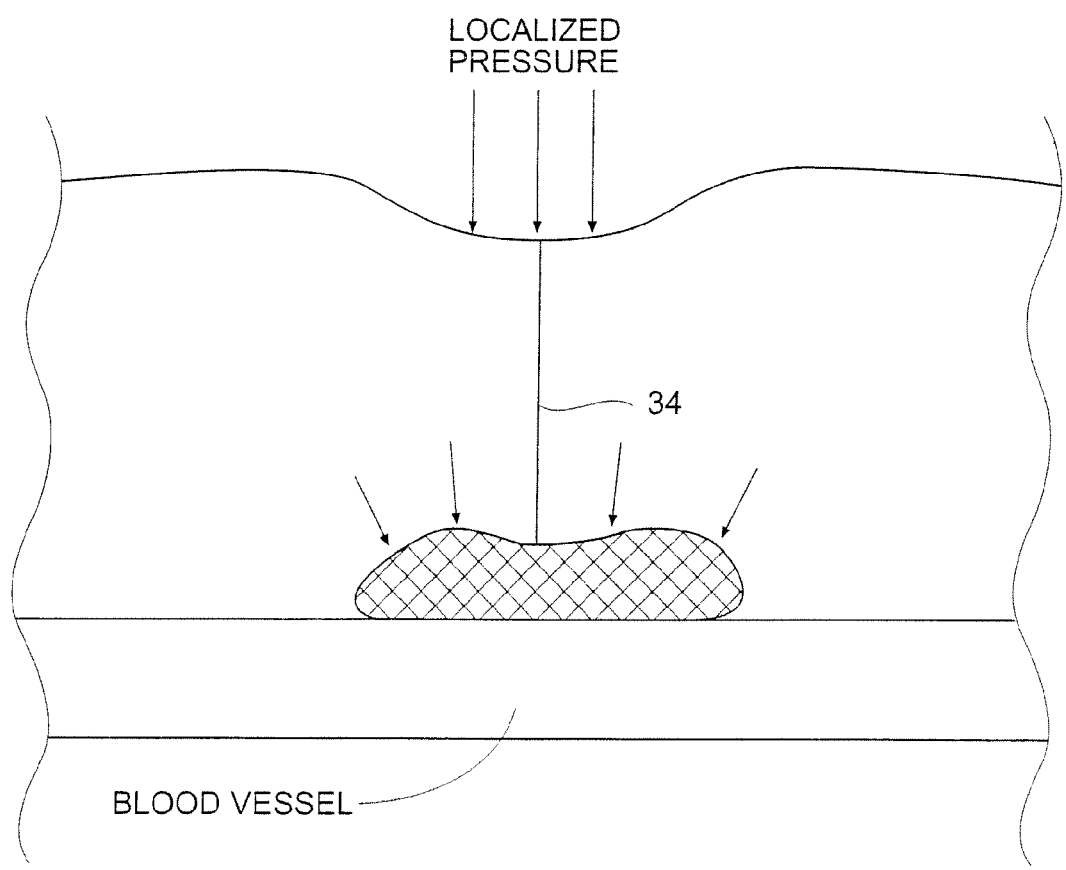
FIG. 6 is a diagrammatic view showing the temporary application of localized pressure to the skin surface as the formative components cross-link to close the vascular puncture site.

At this point, the physician collapses the balloon 38 and withdraws the catheter 30 and guide wire from the tissue track 34. As FIG. 6 shows, the physician now simultaneously applies localized and temporary compression to the skin surface surrounding the tissue track 34.

The application of localized pressure serves two purposes. It is not to prevent blood flow through the tissue track 34, as cross-linking of the components has already proceeded to create a semi-solid gel having sufficient cohesive and adhesive strength to impede blood flow from the puncture site 32. Rather, the localized pressure serves to compress the tissue mass about the semi-solid gel mass. This compression brings the semi-solid gel mass into intimate contact with surrounding tissue mass, while the final stages of cross-linking and gelation take place.

Under localized compression pressure, the electrophilic component 10 and the nucleophilic component 12 are placed in close proximity, to complete their cross-linking and to fully develop cohesive strength. Any remnant catheter track existing through the gel mass will also be closed in this process.

Under localized compression pressure, surface contact between electrophilic component 10 and tissue is also increased, to promote the cross-linking reaction with nucleophilic groups in the surrounding tissue mass. Adhesive strength between the gel mass and tissue is thereby allowed to fully develop, to firmly adhere the gel mass to the surrounding tissue as the solid composition 16 forms in situ.

During this stage, blood will also contact the vessel-side, exposed portion of the gel mass, which now covers the tissue puncture site 32. The electrophilic component 10 will absorb nucleophilic proteins present in the blood, forming a biocompatible surface on the inside of the vessel.

The Localized Compression Stage (The Composition Semi-Solid (Gel) Phase) preferably last about 10 to 40 seconds from the time the physician withdraws the catheter 30.

C. The Hemostasis Stage

The Composition Solid Stage

At the end of the Localized Compression Stage (see FIG. 6), the composition 16 has formed. Hemostasis has been achieved. The individual is free to ambulate and perform normal day-to-day functions.

The mechanical properties of the composition 16 are such to form a mechanical barrier. The composition 16 is well tolerated by the body, without invoking a severe foreign body response.

The mechanical properties of the hydrogel are controlled, in part, by the number of crosslinks in the hydrogel network as well as the distance between crosslinks. Both the number of crosslinks and the distance between crosslinks are dependent on the functionality, concentration, and molecular weight of the polymer and the protein.

Functionality, or the number of reactive groups per molecule, affects the mechanical properties of the resulting hydrogel by influencing both the number of and distance between crosslinks. As discussed previously, the utility of a given polymer significantly increases when the functionality is increased to be greater than or equal to three. The observed incremental increase in functionality occurs when the functionality is increased from two to three, and again when the functionality is increased from three to four. By increasing the functionality of the polymer or protein at a constant concentration, the concentration of crosslinking groups available for reaction are increased and more crosslinks are formed. However, increased mechanical properties cannot be controlled with functionality alone. Ultimately, the steric hindrances of the protein or polymer to which the reactive groups are attached predominate and further changes in the mechanical properties of the hydrogel are not observed. The effect of functionality is saturated when the functionality reaches about four.

The concentration of the protein and polymer also affect the mechanical properties of the resulting hydrogel by influencing both the number of and distance between crosslinks. Increasing the protein and polymer concentration increases the number of available crosslinking groups, thereby increasing the strength of the hydrogel. However, decreases in the elasticity of the hydrogel are observed as the concentration of the protein and polymer is increased. The effects on the mechanical properties by concentration are limited by the solubility of the protein and polymer.

The polymer and protein molecular weight affects the mechanical properties of the resulting hydrogel by influencing both the number of and distance between crosslinks. Increasing the molecular weight of the protein and polymer decreases the number of available crosslinking groups, thereby decreasing the strength of the hydrogel. However, increases in the elasticity of the hydrogel are observed with increasing molecular weight of the protein and polymer. Low molecular weight proteins and polymers result in hydrogels that are strong, but brittle. Higher molecular weight proteins and polymers result in weaker, but more elastic gels. The effects on the mechanical properties by molecular weight are limited by the solubility of the protein and polymer. However, consideration to the ability of the body to eliminate the polymer should be made, as large molecular weight polymers are difficult to clear.

D. The Degradation Stage

The Composition Re-Absorption Stage

Over a controlled period, the material composition 16 is degraded by physiological mechanisms. Histological studies have shown a foreign body response consistent with a biodegradable material, such as VICRYL™ sutures. As the material is degraded, the tissue returns to a quiescent state. The molecules of the degraded genus hydrogel composition are cleared from the bloodstream by the kidneys and eliminated from the body in the urine. In a preferred embodiment of the invention, the material loses its physical strength during the first fifteen days, and totally resorbs in about four weeks.

The features of the invention are set forth in the following claims.

I claim:

1. A method comprising:
mixing a first electrophilic polymer material comprising poly(ethylene glycol) having a functionality of greater than or equal to three and a second electrophilic polymer material comprising a linear polymer with a solution comprising recombinant serum albumin having a concentration of about 25% by weight or less and a buffer material comprising tris-hydroxymethylaminomethane, said buffer material being capable of providing a reaction pH range of between about 8 to about 10, and
applying the mixture to a tissue region, wherein the first electrophilic polymer material and the second electrophilic polymer material crosslink with the recombinant serum albumin to form a mechanical barrier.

2. A method according to claim 1, wherein the first electrophilic polymer material has a molecular weight of 10,500±1500.

3. A method according to claim 1, wherein the buffer material further comprises carbonate.

4. A method according to claim 3, wherein the solution comprising the recombinant serum albumin has a pH of between 8.3 and 8.5 prior to mixing with the first component.

5. The method of claim 1, wherein the first electrophilic polymer comprises poly(ethylene glycol) (PEG) having a molecular weight of between 9,000 and 12,000.

6. The method of claim 1, wherein the second electrophilic polymer comprises a linear polymer having a functionality of at least three.

7. The method of claim 1, wherein the first electrophilic polymer and the second electrophilic polymer each individually comprise a hydrolytically degradable moiety.

8. The method of claim 7, wherein the hydrolytically degradable moiety comprises saturated di-acids, unsaturated di-acids, poly(glycolic acid), poly(DL-lactic acid), poly(L-lactic acid), poly(ξ-caprolactone), poly(δ-valerolactone), poly(γ-butyrolactone), poly(amino acids), poly(anhydrides), poly(orthoesters), poly(orthocarbonates), poly(phosphoesters), or derivatives thereof.

9. The method of claim 7, wherein the hydrolytically degradable moiety comprises glutarate, poly(DL-lactic acid), poly(L-lactic acid), or a combination thereof.

10. The method of claim 1, wherein the first electrophilic polymer and the second electrophilic polymer each individually comprise N-hydroxysuccinimide.

11. The method of claim 1, further comprising preparing a solution comprising of the first electrophilic polymer and the second electrophilic polymer.

12. The method of claim 11, wherein the solution comprises from 5 w/w % to 35 w/w % of the first electrophilic polymer and the second electrophilic polymer.

13. The method of claim 11, wherein the solution further comprises sterile water.

14. The method of claim 11, wherein the polymer solution comprises at least 50% by weight or more of the first electrophilic polymer.

* * * * *

```
SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: An enzymatically degradable, collaganese
      sensitive linkage
<220> FEATURE:
<221> NAME/KEY: UNSURE
<222> LOCATION: (1)..(4)

<400> SEQUENCE: 1

Leu Gly Pro Ala
1
```